US00PP33208P2

(12) United States Plant Patent
Hochberg

(10) Patent No.: US PP33,208 P2
(45) Date of Patent: Jun. 29, 2021

(54) ***LAGERSTROEMIA* PLANT NAMED 'HOCH631'**

(50) Latin Name: *Lagerstroemia indica*
Varietal Denomination: HOCH631

(71) Applicant: Hochberg Ornamental Export Plants Ltd, Moshav Bitzaron (IL)

(72) Inventor: Omer Hochberg, Moshav Bitzaron (IL)

(73) Assignee: Hochberg Ornamental Export Plants Ltd

( * ) Notice: Subject to any disclaimer, the term of this patent is extended or adjusted under 35 U.S.C. 154(b) by 0 days.

(21) Appl. No.: 17/094,132

(22) Filed: Nov. 10, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct cultivar of *Lagerstroemia* plant named 'HOCH631' is disclosed, characterized by red-purple flowers, and black foliage. Plants are upright in form and produce new flowers and flower buds throughout Summer. The new variety is a *Lagerstroemia*, normally used for outdoor ornamental purposes.

1 Drawing Sheet

Latin name of the genus and species: *Lagerstroemia indica.*

Variety denomination: 'HOCH631'.

BACKGROUND OF THE INVENTION

The new *Lagerstroemia* cultivar is a product of a planned breeding program conducted by the inventor, in Moshav Bitzaron, Israel. The objective of the breeding program was to develop new Crepe Myrtle plants for ornamental purposes. The cross resulting in this new variety was made during July of 2014.

The seed parent is the unpatented proprietary variety referred to as *Lagerstroemia* 'L54'. The pollen parent is the unpatented proprietary variety referred to as *Lagerstroemia* 'L18'. The new variety was selected in August of 2015 by the inventor in a group of seedlings resulting from the 2014 crossing, in a nursery in Moshav Bitzaron, Israel. Date of first sale was Jan. 1, 2020, occurring in Europe. This sale was made directly by the inventor or one who obtained the claimed invention directly or indirectly from the inventor. This sale and all public disclosures made between Jan. 1, 2020 and the filing of this application fall within the exception allowed under 102(b)(1).

Asexual reproduction of the new cultivar was performed by softwood cuttings. This was first performed at the same nursery in Moshav Bitzaron, Israel during June of 2016, and has shown that the unique features of this cultivar are stable and reproduced true to type in multiple successive generations.

SUMMARY OF THE INVENTION

The cultivar 'HOCH631' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOCH631' These characteristics in combination distinguish 'HOCH631' as a new and distinct *Lagerstroemia* cultivar:

1. Red-purple blooms.
2. Black foliage.
3. Continuous bud and flower formation throughout the Summer.
4. Upright plant habit, reaching 70 to 90 cm in the second year.

PARENT COMPARISON

Plants of the new cultivar 'HOCH631' are similar to plants of the seed parent in most horticultural characteristics; however, plants of the new cultivar 'HOCH631' differ in the following;

1. The new variety has red-purple flowers, while the seed parent has light pink flowers.

Plants of the new cultivar 'HOCH631' are similar to plants of the pollen parent in most horticultural characteristics; however, plants of the new cultivar 'HOCH631' differ in the following;

1. The new variety has red-purple flowers, while the pollen parent has red flowers.
2. The new variety has an upright plant form; the pollen parent is mounding.
3. Foliage of the new variety is black; foliage of the pollen parent is green.

COMMERCIAL COMPARISON

Plants of the new cultivar 'HOCH631' are comparable to the commercial variety *Lagerstroemia* 'Best Red', unpatented. The two *Lagerstroemia* varieties are similar in most horticultural characteristics; however, the new variety 'HOCH631' differs in the following;

1. The new variety has red-purple blooms; this comparator has red blooms.
2. The new variety produces new flowers and buds during approximately 10 weeks of Summer, this comparator has a single bloom emergence.
3. Plants of the new variety begin flowering about three weeks earlier than plants of this comparator.

Plants of the new cultivar 'HOCH631' are comparable to the commercial variety *Lagerstroemia* 'WHIT VIII', U.S. Plant Pat. No. 16,616. The two *Lagerstroemia* varieties are similar in most horticultural characteristics; however, the new variety 'HOCH631' differs in the following;

1. The new variety has red-purple blooms, while this comparator has pink blooms.
2. The new variety has black foliage; this comparator has green foliage.

BRIEF DESCRIPTION OF THE PHOTOGRAPH

The accompanying photograph illustrates two typical flowering plants of 'HOCH631' grown outdoors in Moshav Bitzaron, Israel. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'HOCH631' plants grown outdoors during 2019 and 2020, in Visalia, Calif. The growing temperature ranged from approximately 18° C. to 38° C. during the day and from approximately 5° C. to 10° C. during the night. General light conditions are normal sunlight and numerical values represent averages of typical plant types. Measurements were taken during June of 2020.

Botanical classification: *Lagerstroemia indica* 'HOCH631'.

PROPAGATION

Type of propagation typically used: Softwood cuttings.
Time to initiate roots: 21 days at 18-27° C.
Time to produce a rooted cutting: 1-2 months at 18-27° C.
Root description: Thin fibrous, dense, moderate branching. White in color, not accurately measured with R.H.S. Chart.

PLANT

Age of plant described: About 1.5 years old from a rooted cutting.
Container size: 3 gallon container.
Growth habit: Upright.
Plant spread: 40 cm.
Plant height: 65 cm.
Plant vigor: Very good.
Length of primary lateral branches: Varies as the plant is often pruned. 20 to 40 cm on average.
Diameter of lateral branches: 4 to 7 mm.
Quantity of lateral branches: About 10 to 14.

Stem:
- *Color*.—New growth: Near RHS Greyed-Purple 187A. Old growth: Near RHS Greyed-Purple N187D striated 187A.
- *Shape*.—Round.
- *Strength*.—Good, flexible.
- *Aspect angle*.—Upright.
- *Texture*.—Very slightly pubescent on youngest growth, striated with age.

Internode length: Average range 1.4 to 1.8 cm.
Bark peel: Not observed.

FOLIAGE

Leaf:
- *Arrangement*.—Sub-opposite.
- *Average length*.—4.5 cm.
- *Average width*.—2.5 cm.
- *Shape of blade*.—Ovate.
- *Apex*.—Acute.
- *Base*.—Obtuse.
- *Margin*.—Entire.
- *Aspect*.—Strongly undulate
- *Texture of top surface*.—Smooth. Glossy.
- *Texture of bottom surface*.—Smooth. Matte.
- *Color*.—Young foliage upper side: Near RHS Greyed-Purple N186A. Young foliage under side: Near RHS Greyed-Purple N186C. Mature foliage upper side: Near RHS Black 202A. Mature foliage under side: Near RHS Greyed-Purple 187A to Black 202A. Venation: Type: Pinnate. Venation color upper side: Near RHS Greyed-Purple N186B. Venation color under side: Near RHS Greyed-Purple N186C.
- *Petiole*.—Not present, sessile.

FLOWER

Natural flowering season: Summer through Fall. Begins flowering mid-June in California.
Inflorescence form: Panicles.
Flowers per inflorescence: About 40 to 60 flowers and buds.
Inflorescence size:
- *Width*.—13 cm.
- *Length*.—Average 12 cm.

Individual flowers:
- *Type*.—Rotate.
- *Shape*.—Obovate.
- *Habit*.—Whorled outward.
- *Diameter*.—4.7 cm.
- *Depth*.—1.7 cm.
- *Persistence*.—Self-cleaning.
- *Fragrance*.—Faint earthy scent.

Petals:
- *Arrangement*.—Whorled.
- *Number*.—6.
- *Shape*.—Overall irregular orbicular.
- *Aspect*.—Deeply undulate.
- *Margin*.—Deeply ruffled, crenate.
- *Tip shape*.—Rounded.
- *Base shape*.—Rounded.
- *Length*.—2.0 cm, undulated, cannot unfold.
- *Width*.—1.5 cm, undulated, cannot unfold.
- *Texture*.—Upper: Glabrous. Lower: Glabrous.
- *Color*.—When opening: Upper surface: Near RHS Red-Purple 71A. Under surface: Near RHS Red- Purple 71A. Fully opened: Upper surface: Near RHS Red-Purple 71B. Under surface: Near RHS Red-Purple 61B.

Bud:
*Shape*.—Sphere.
*Length*.—7 mm.
*Diameter*.—7 mm.
*Color*.—Near RHS Greyed-Purple 187B, flushed 187A.
*Appearance*.—Very glossy.

Calyx:
*Shape*.—Fused into a conical shape.
*Length*.—16 mm.
*Diameter*.—10 mm.

Sepals:
*Appearance*.—Glossy exterior, matte interior.
*Arrangement*.—Rotate, fused.
*Shape*.—Deltate.
*Tip shape*.—Acute.
*Base shape*.—Obtuse.
*Margin*.—Entire.
*Quantity per flower*.—6.
*Length*.—15 mm.
*Width*.—5 mm.
*Margin*.—Entire.
*Texture*.—Inner: Smooth. Outer: Smooth.
*Color*.—Inner: Near RHS Greyed-Purple 186C. Base near Yellow-Green 145D. Outer: Near RHS Greyed-Purple 187B apex 187A.

Peduncle:
*Length*.—Average range 1.5 to 2.0 cm.
*Diameter*.—4 mm.
*Texture*.—Glabrous.
*Color*.—Near RHS Greyed-Purple 187A.
*Orientation*.—Upright.
*Strength*.—Strong.

Pedicel:
*Length*.—5 to 7 mm.
*Diameter*.—2 mm.
*Angle*.—About 45 degrees from attachment.
*Strength*.—Moderate.
*Texture*.—Slightly pubescent.
*Color*.—Near Greyed-Purple N186B.

REPRODUCTIVE ORGANS

Stamens:
*Number*.—About 30, curled and congested.
*Filament length*.—About 7 mm, when pulled straight.
*Filament color*.—Near Red-Purple 61C.

Anthers:
*Shape*.—Ovate.
*Length*.—1 mm.
*Color*.—Yellow 12C.
*Pollen*.—Not observed.

Pistil:
*Number*.—1.
*Length*.—1.9 cm.

Stigma:
*Shape*.—Globular.
*Color*.—Near RHS Greyed-Purple N187A.
*Ovary color*.—Near RHS Yellow 2D.

OTHER CHARACTERISTICS

Fruits and seeds: Not observed to date.

Disease/pest resistance: Neither resistance nor susceptibility to normal diseases and pests of *Lagerstroemia* observed.

Temperature range: Observed to tolerate a temperature range from −28° C. to 35° C. Root hardy to −28 C, top of the plant does die back to the ground.

What is claimed is:

1. A new and distinct cultivar of *Lagerstroemia* plant named 'HOCH631' as herein illustrated and described.

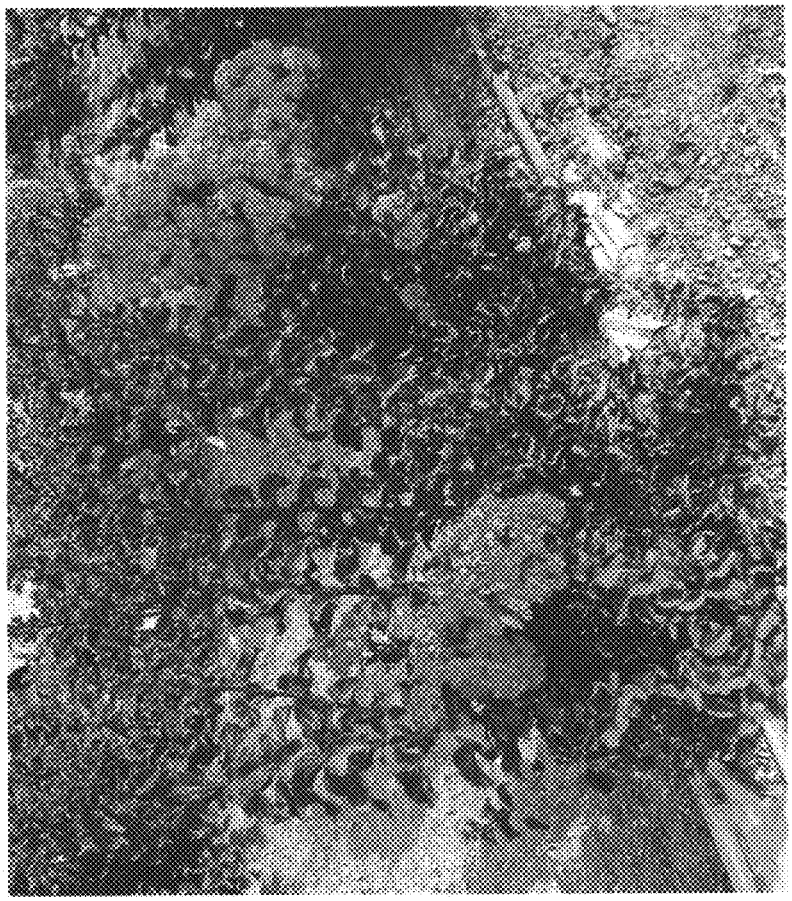

* * * * *